(12) United States Patent
Bui et al.

(10) Patent No.: US 8,778,316 B2
(45) Date of Patent: *Jul. 15, 2014

(54) NON-STICKY, HYDRATING AND MOISTURIZING AQUEOUS LIP GLOSS COMPOSITION

(75) Inventors: Hy Si Bui, Piscataway, NJ (US); Mohamed Kanji, Edison, NJ (US); Luis Ortega, Englewood, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/139,207

(22) PCT Filed: Dec. 11, 2009

(86) PCT No.: PCT/US2009/067718
§ 371 (c)(1),
(2), (4) Date: Aug. 26, 2011

(87) PCT Pub. No.: WO2010/068894
PCT Pub. Date: Jun. 17, 2010

(65) Prior Publication Data
US 2011/0300090 A1   Dec. 8, 2011

Related U.S. Application Data

(60) Provisional application No. 61/121,597, filed on Dec. 11, 2008.

(51) Int. Cl.
*A61K 8/00* (2006.01)
*A61K 31/74* (2006.01)

(52) U.S. Cl.
USPC ........ 424/64; 424/401; 424/78.03; 424/78.08

(58) Field of Classification Search
USPC .................................................. 424/401, 64
See application file for complete search history.

(56) References Cited

U.S. PATENT DOCUMENTS

| | | | |
|---|---|---|---|
| 2,957,838 A | 10/1960 | Mills, Jr. | |
| 4,226,889 A | 10/1980 | Yuhas | |
| 5,032,391 A | 7/1991 | Helioff et al. | |
| 5,618,524 A | 4/1997 | Bolich, Jr. et al. | |
| 5,744,129 A * | 4/1998 | Dobbs et al. | 424/61 |
| 5,998,547 A | 12/1999 | Hohner | |
| 6,039,960 A | 3/2000 | Chung et al. | |
| 6,280,753 B1 | 8/2001 | Chung et al. | |
| 6,492,455 B1 | 12/2002 | Nadolsky | |
| 6,524,564 B1 | 2/2003 | Kim et al. | |
| 2004/0186308 A1 | 9/2004 | Koch et al. | |
| 2004/0223986 A9 | 11/2004 | Boussouira et al. | |
| 2005/0013992 A1 | 1/2005 | Azad et al. | |
| 2005/0201965 A1 | 9/2005 | Kuhlman et al. | |
| 2006/0188459 A1 | 8/2006 | Heinrichs et al. | |
| 2006/0204460 A1 * | 9/2006 | Takeda et al. | 424/64 |
| 2007/0031361 A1 * | 2/2007 | Herrmann et al. | 424/70.11 |
| 2007/0110700 A1 | 5/2007 | Wells et al. | |
| 2007/0110702 A1 | 5/2007 | Ehara | |
| 2008/0031842 A1 | 2/2008 | Kuhlman et al. | |
| 2008/0207871 A1 | 8/2008 | Seiler et al. | |
| 2009/0035244 A1 | 2/2009 | Rando et al. | |
| 2011/0031361 A1 * | 2/2011 | Garvin | 248/213.2 |

FOREIGN PATENT DOCUMENTS

| | | |
|---|---|---|
| DE | 100 64 799 | 6/2002 |
| DE | 103004008941 | 9/2005 |
| EP | 2 036 536 | 3/2009 |
| WO | WO 96/03967 | 2/1996 |
| WO | WO 01/17485 | 3/2001 |
| WO | WO 02/088456 A1 | 11/2002 |
| WO | WO 2006/112690 | 10/2006 |
| WO | WO 2006/127883 | 11/2006 |
| WO | WO 2007/048672 | 5/2007 |
| WO | 2007 096400 | 8/2007 |
| WO | WO 2007/139812 | 12/2007 |
| WO | WO 2008/046763 | 4/2008 |
| WO | WO 2009/085888 | 7/2009 |

OTHER PUBLICATIONS

Poucher's Perfumes, Cosmetics and Soaps, (10th ed. by Hilda Butler), Kluwer Academic Publishers, p. 422.*
Cosmetic Business 2008 Conference Program.*
U.S. Appl. No. 13/139,171, filed Jul. 29, 2011, Bui, et al.
U.S. Appl. No. 13/133,688, filed Aug. 8, 2011, Bui, et al.
U.S. Appl. No. 13/139,149, filed Jun. 10, 2011, Bui, et al.
U.S. Appl. No. 13/133,599, filed Aug. 26, 2011, Bui, et al.
International Search Report Issued Aug. 18, 2010 in PCT/US09/067718 filed Dec. 11, 2009.
Bergbreiter et al., Tit. Lett., 1997, 38 (21), 3703-3706.
http://www.Chemical Book.com/ChemicalProductProperty_EN_CB3748204.htm, Poly(methyl vinyl ether-alt-maleic anhydride), 2010.

* cited by examiner

*Primary Examiner* — Gina C Justice
(74) *Attorney, Agent, or Firm* — Oblon, Spivak, McClelland, Maier & Neustadt, L.L.P.

(57) ABSTRACT

The present invention is directed to a non-sticky, hydrating and moisturizing aqueous lip gloss having: (a) at least one alkyl ethoxylated polymer wax; (b) at least one oil soluble polar modified polymer; (c) water; (d) at least one non volatile oil capable of solubilizing the polar modified polymer; and (e) optionally, at least one colorant, and wherein the composition does not require silicone fluids therein.

19 Claims, No Drawings

NON-STICKY, HYDRATING AND MOISTURIZING AQUEOUS LIP GLOSS COMPOSITION

FIELD OF THE INVENTION

The present invention generally relates to a novel moisturizing lip gloss composition. More particularly, the present invention relates to a lip gloss composition having high gloss and being capable of both hydrating and moisturizing the lips, without requiring the use of silicone fluids.

BACKGROUND OF THE INVENTION

The problem with conventional lip glosses is their inability to continuously hydrate and moisturize the lips. The reason for this is that in order to continuously hydrate and moisturize the lips, water either has to be deposited onto the lips from the gloss itself or drawn to the lips from the atmosphere. In the event that the source of water for hydration is the product itself, it is very difficult to maintain the water in a stabilized form. Failure to do so results in the water quickly evaporating from the surface of the lips leaving the lips feeling dry as opposed to hydrated and moisturized.

Also, conventional lip gloss compositions which impart a high degree of gloss onto the lip surface require the presence of silicone fluids in the composition. Silicone fluids are known to high refractive indices which provide shine. These types of silicone fluids, however, have poor environmental profiles and, because they are relatively expensive, add to the cost of goods.

Therefore, it is an object of the present invention to provide a lip gloss composition, having a high degree of gloss, which is capable of both hydrating and moisturizing the lips in a continuous manner, in the absence of silicone fluids.

BRIEF SUMMARY OF THE INVENTION

In a first embodiment of the present invention, A composition comprises: (a) at least one alkyl ethoxylated polymer wax; (b) at least one oil soluble polar modified polymer; (c) water; (d) at least one non-volatile oil capable of solubilizing the polar modified polymer; and (e) optionally, at least one colorant, and wherein the composition does not require silicone fluids therein.

Another embodiment of the present invention is directed to a method of simultaneously imparting gloss, non-sticky, hydration and moisturization onto lips by applying the above-disclosed composition onto the lips.

It has surprisingly been discovered that the above-described composition results in the formation of a stable emulsion capable of imparting high gloss onto the lips, in the absence of any conventional silicone fluids used to provide shine. Moreover, there is no longer a need for using surfactant/emulsifiers to form the stable emulsion. Finally, the resultant composition, when applied onto the lips, both hydrates and moisturizes the lips dues to the large amount of water entrapped therein, while at the same time making the lips feel unusually refreshed and pleasant.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

Alkyl Ethoxylated Polymer Wax

The compositions of the present invention comprise at least one alkyl ethoxylated polymer that may be selected from di-alkyl, tri-alkyl- and combinations of di-alkyl and tri-alkyl substituted alkyl ethoxylated polymers. Alternatively mono-alkyl, di-alkyl, tri-alkyl, tetra-alkyl and all combinations thereof substituted alkyl ethoxylated polymers. The alkyl group can be saturated or unsaturated, branched or linear and contain a number of carbon atoms from about 12 carbon atoms to about 50 carbon atoms.

The alkyl substitution of the alkyl ethoxylated polymer includes mono-alkyl, di-alkyl, tri-alkyl and tetra-alkyl substitution of the polymer and combinations thereof. Examples of the polymers that are mono alkyl substituted include: Steareth-100 available as Brij 700 from Uniqema Inc., Pareth alcohols available as Performathox 450, 480 and 490 available from New Phase Technologies, Inc. The di-alkyl substituted polymers include PEG 120 methyl glucose dioleate available as Glutamate DOE-120 and Glucamate DOE-120 both from Chemron Corporation. The tri-alkyl substituted polymers include PEG 120 methyl glucose trioleate available as Glucamate LT from Chemron Corporation. The tetra-alkyl substituted polymers include PEG 150 pentaerythrityl tetrastearate available as Crothix from Croda Corporation.

In the present invention, preferred alky ethoxylated polymers include ethoxylated $C_{20-50}$ fatty alcohols having an average molecular weight of the alcohol chain of from about 450 to 550 and an average degree of ethoxylation of from about 2.5 to 95. These alkyl ethoxylated waxes have a melting point ranging from 70 to 100° C. The most preferred waxes are Pareth-10 alcohol which is a mixture of $C_{20-40}$ fatty alcohols having an average molecular weight of about 450 and average degree of ethoxylation of about 10, commercially available as Performathox 450, and Pareth-40 alcohol, which is a mixture of $C_{20-40}$ fatty alcohols having an average molecular weight of about 450 and an average degree of ethoxylation of about 42, commercially available as Performathox 480, both from New Phase Technologies, Inc.

Preferably, the alkyl ethoxylated wax(es) represent from about 1% to about 30% by weight of the total weight of the composition, more preferably from about 5% to about 20% by weight of the total weight of the composition, and most preferably from about 7% to about 15% by weight of the total composition, including all ranges and subranges therebetween.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the polar modified polymer(s) represent from about 1% to about 30% of the total weight of the composition, more preferably from about 3% to about 20% of the total weight of the composition, and most preferably from about 5% to about 15%, including all ranges and subranges therebetween.

In other embodiments of the present invention, the oil soluble polar modified polymer is present in the composition of the invention in an amount ranging from about 3% to about 30% by weight, such as from about 7% to about 20% by weight, and from about 10% to about 50% by weight, including all ranges and subranges therebetween, all weights based on the total weight of the composition.

Reaction Product

According to preferred embodiments of the present invention, the oil-soluble polar modified polymer is reacted with the alkyl ethoxylated polymer wax, in the presence of oil to form a first reaction product. If the reaction is conducted at a relatively high temperature (for example, above 140° C.) and for a long period of time (>5 hours), a significant amount of the hydrophilic group (for example, carboxylic acid group associated with maleic anhydride groups) of the oil soluble polar modified polymer reacts with hydroxyl group(s) of the alkyl ethoxylated wax to yield a significant amount of the reaction product. If, however, the reaction is conducted at a relatively low temperature (for example, below 100° C.) and for a short period of time (<1 hour), only a small portion of the hydrophilic group of the polar modified polymer reacts with hydroxyl group(s) of the alkyl ethoxylated polymer wax to yield a minor amount of reaction product. Depending upon desired application, a minor amount or a significant amount of the first reaction product may be desired.

Non-Volatile Oil Capable of Solubilizing the Polar Modified Polymer

The cosmetic compositions of the present invention comprise at least one non-volatile oil capable of solubilizing the polar modified polymer. As used herein, the term "non-volatile" means having a boiling point of greater than about 100 degrees C. The at least one non-volatile solvent typically comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol; and mixtures thereof.

The at least one non-volatile solvent for the oil soluble polar modified polymer is present in the cosmetic composition of the invention in an amount of from about 30% to about 90% by weight, such as from about 40% to about 80% by weight, including all ranges and subranges therebetween, such as from about 50% to about 70% by weight, all weights based on the total weight of the composition.

Water

The composition of the present invention also comprises water in order to form a water-in-oil emulsion. The water is typically present in an amount of from about 5% to about 50% by weight, such as from about 15% to about 45% by weight, such as from about 25% to about 40% by weight, including all ranges and subranges therebetween, all weights based on the total weight of the composition.

Optional Ingredients

The composition of the present invention may also include any one, or more, optional ingredients. Examples thereof include, but are not limited to, colorants such as pigments and dyestuffs, co-solvents, plasticizers, preservatives, fillers, active ingredients, additional waxes and sunscreens.

It has surprisingly been discovered that the association of an alkyl ethoxylated polymer with the above-described oil soluble polar modified polymer results in the formation of a stable emulsion capable of imparting high gloss onto the lips, in the absence of any conventional silicone fluids used to provide shine. Moreover, the use of the alkyl ethoxylated polymer eliminates the need for using surfactant/emulsifiers to form the stable emulsion. Finally, the resultant composition, when applied onto the lips, both hydrates and moisturizes the lips dues to the large amount of water entrapped therein, while at the same time making the lips feel unusually refreshed and pleasant.

The present invention is further described in terms of the following non-limiting examples. Unless otherwise indicated, all parts and percentages are on a weight-by-weight percentage basis.

EXAMPLES

Example 1

Hydrating/Moisturizing Lip Gloss

| Phase | INCI Name | |
|---|---|---|
| A1 | Octododecyl Neopentanoate | 28.00 |
| A1 | Performathox 450 | 8.00 |
| A1 | polypropylene-ethylene-maleic anhydride copolymer wax | 8.00 |
| A2 | Pigments | 3.41 |
| A2 | C18-36 Triglyceride | 3.41 |
| B1 | Deionized Water | 47.18 |
| B1 | glycerin | 2.00 |
| | Total | 100 |

Procedure:
1. Heated the oil of phase A in a Beaker 1 at 95 Celsius degrees.
2. Added the polypropylene-ethylene-maleic anhydride copolymer wax into beaker 1 containing the oil to dissolve.
3. When the polypropylene-ethylene-maleic anhydride copolymer wax was totally dissolved, added Performathox 450 and melted until the solution was homogeneous.
4. Added pigment grind A2 into beaker 1 and stirred well until wax was dispersed.
5. Reduced the temperature of beaker 1 to 85 Celsius degrees.
6. Used the Silverson to mix the phase A content in beaker 1 while maintaining the temperature at 85-90 Celsius degrees.
7. In a separate beaker 2, added the glycerin into hot water at 85 Celsius degrees and stirred well.
8. Added dropwise the water solution of part B into the beaker 1 while the speed of Silverson was increased to 9000 rpm.
9. Left Silverson@ 9000 rpm for 30 minutes, after that reduced speed to 2000 rpm for 5 mins.
10. Reduced temperature of the mixture to room temperature.
11. Poured mixture to the container.

Example 2

| PHASE | INCI NAME | |
|---|---|---|
| A1 | Octododecanol | 4.20 |
| A1 | Octyldodecyl Neopantanoate | 10.00 |
| A1 | Hydrogenated Polydecene | 9.62 |
| A1 | Hydrogenated Polydecene | 5.00 |
| A1 | Performathox 480 | 4.00 |
| A1 | Polypropylene-ethylene-maleic acid anhydride copolymer wax in Isohexadecane | 13.33 |
| A1 | VP/Eicosene Copolymer | 3.00 |
| A2 | Shade RD513 | 9.35 |
| B2 | Deionized Water | 40.00 |
| B2 | Caprylic Glycol | 0.50 |
| B2 | Pentylene Glycol | 1.00 |
| | Total | 100.00 |

Procedure:

See Example 1.

What is claimed is:

1. A composition comprising:
   (a) a reaction product comprising (i) at least one alkyl ethoxylated polymer wax and (ii) at least one oil-soluble polar modified polymer comprising at least one C2-C4 monomer, modified with at least one hydrophilic unit, and having a melting point above 75° C.,
   (b) water; and
   (c) at least one non-volatile oil capable of solubilizing the polar modified polymer,
   wherein the composition is in the form of an emulsion.

2. The composition of claim 1, wherein the alkyl ethoxylated polymer wax is derived from a Pareth-10 alcohol.

3. The composition of claim 1, wherein the alkyl ethoxylated polymer wax is present in an amount of from about 1 to about 30% by weight, based on the weight of the composition.

4. The composition of claim 1, wherein the oil-soluble polar modified polymer is present in an amount of from about 3 to about 30% by weight, based on the weight of the composition.

5. The composition of claim 1, wherein water is present in an amount of from about 5 to about 50% by weight, based on the weight of the composition.

6. The composition of claim 1, wherein the non-volatile oil is present in an amount of from about 30 to about 90% by weight, based on the weight of the composition.

7. A method of simultaneously imparting gloss, non-sticky, hydration and moisturization onto lips comprising applying onto lips the composition of claim 1.

8. A method of simultaneously imparting gloss, non-sticky, hydration and moisturization onto lips comprising applying onto lips the composition of claim 2.

9. A method of simultaneously imparting gloss, non-sticky, hydration and moisturization onto lips comprising applying onto lips the composition of claim 3.

10. A method of simultaneously imparting gloss, non-sticky, hydration and moisturization onto lips comprising applying onto lips the composition of claim 4.

11. A method of simultaneously imparting gloss, non-sticky, hydration and moisturization onto lips comprising applying onto lips the composition of claim 5.

12. A method of simultaneously imparting gloss, non-sticky, hydration and moisturization onto lips comprising applying onto lips the composition of claim 6.

13. The composition of claim 1, further comprising at least one colorant.

14. The composition of claim 1, wherein the composition is free of silicone fluid.

15. The composition of claim 1, wherein the melting point of the oil-soluble polar modified polymer is between 90° C. and 160° C.

16. The composition of claim 1, wherein the at least one hydrophilic unit of the oil-soluble polar modified polymer is maleic anhydride.

17. The composition of claim 1, wherein the oil-soluble polar modified polymer has from about 0.5% to about 10% hydrophilic units.

18. The composition of claim 1, wherein the oil-soluble polar modified polymer has from about 1% to about 8% hydrophilic units.

19. The composition of claim 1, wherein the oil-soluble polar modified polymer is a polypropylene and/or polyethylene homopolymer or copolymer modified with maleic anhydride units.

* * * * *

UNITED STATES PATENT AND TRADEMARK OFFICE
CERTIFICATE OF CORRECTION

PATENT NO. : 8,778,316 B2  
APPLICATION NO. : 13/139207  
DATED : July 15, 2014  
INVENTOR(S) : Hy Si Bui et al.

Page 1 of 1

It is certified that error appears in the above-identified patent and that said Letters Patent is hereby corrected as shown below:

In the Claims

Column 9, line 9, Claim 1, "75° C.," should read --75° C,--.

Column 10, line 18, Claim 15, "90° C." should read --90° C--.

Signed and Sealed this  
Twenty-eighth Day of October, 2014

Michelle K. Lee  
*Deputy Director of the United States Patent and Trademark Office*